US009721133B2

(12) United States Patent
Trajkovic et al.

(10) Patent No.: US 9,721,133 B2
(45) Date of Patent: Aug. 1, 2017

(54) IMAGING BARCODE SCANNER FOR ENHANCED DOCUMENT CAPTURE

(71) Applicant: SYMBOL TECHNOLOGIES, INC., Lincolnshire, IL (US)

(72) Inventors: Miroslav Trajkovic, East Setauket, NY (US); Bradley S Carlson, Huntington, NY (US); Duanfeng He, South Setuaket, NY (US)

(73) Assignee: Symbol Technologies, LLC, Holtsville, NY (US)

( * ) Notice: Subject to any disclaimer, the term of this patent is extended or adjusted under 35 U.S.C. 154(b) by 65 days.

(21) Appl. No.: 14/601,404

(22) Filed: Jan. 21, 2015

(65) Prior Publication Data
US 2016/0210492 A1  Jul. 21, 2016

(51) Int. Cl.
*G06K 7/10* (2006.01)
(52) U.S. Cl.
CPC ....... *G06K 7/1096* (2013.01); *G06K 7/10752* (2013.01)
(58) Field of Classification Search
CPC . G06K 7/1465; G06K 7/10841; G06K 7/1096
USPC .......... 235/435, 462.01, 462.22, 462.32
See application file for complete search history.

(56) References Cited

U.S. PATENT DOCUMENTS

| | | | |
|---|---|---|---|
| 7,389,002 B1 | 6/2008 | Knight | |
| 8,749,620 B1 | 6/2014 | Knight et al. | |
| 2006/0255144 A1* | 11/2006 | Meier | G06K 7/10574 235/454 |
| 2007/0145136 A1* | 6/2007 | Wiklof | G06K 7/10564 235/454 |
| 2010/0103300 A1 | 4/2010 | Jones et al. | |
| 2010/0163627 A1 | 7/2010 | Olmstead | |
| 2010/0283842 A1* | 11/2010 | Guissin | G02B 13/06 348/68 |
| 2012/0118963 A1* | 5/2012 | Drzymala | G06K 7/10722 235/454 |

(Continued)

FOREIGN PATENT DOCUMENTS

| | | |
|---|---|---|
| EP | 108548 A1 | 5/1984 |
| EP | 267734 B1 | 1/1994 |

OTHER PUBLICATIONS

International Search Report and Written Opinion mailed Apr. 15, 2015 in counterpart PCT application PCT/US2015/065726.

*Primary Examiner* — Paultep Savusdiphol

(57) ABSTRACT

An imaging barcode scanner and method are provided. The scanner includes a housing defining a work surface, a window supported by the housing, a first array of photosensitive elements having a first field of view traversing the window and intersecting the work surface at a first angle, and a second array of photosensitive elements having a second field of view traversing the window and intersecting the work surface at a second angle. The scanner also includes a processor connected to the first and second arrays of photosensitive elements, and configured to: receive a first image of the work surface from the first array of photosensitive elements, and a second image of the work surface from the second array of photosensitive elements; register the first image with the second image; and generate an enhanced image of the work surface based on the registered first image and second image, the enhanced image having a greater pixel density than the first image and the second image.

17 Claims, 12 Drawing Sheets

(56) References Cited

U.S. PATENT DOCUMENTS

| | | | |
|---|---|---|---|
| 2013/0092735 A1* | 4/2013 | Liu | G06K 7/10 235/440 |
| 2013/0206839 A1 | 8/2013 | Gao | |
| 2014/0160231 A1 | 6/2014 | Middleton et al. | |
| 2014/0198185 A1* | 7/2014 | Haugen | G06T 7/0008 348/48 |
| 2015/0144693 A1* | 5/2015 | Li | G06K 7/10722 235/437 |

* cited by examiner

IMAGING BARCODE SCANNER FOR ENHANCED DOCUMENT CAPTURE

BACKGROUND OF THE INVENTION

Imaging barcode scanners, such as bioptic scanners, may be employed in environments such as checkout counters to capture images of products and decode barcodes from those images. Other devices referred to generally as imaging document scanners are capable of various scanning operations beyond barcode scanning. Such operations are referred to as document capture operations, and can include, for example, extracting features (e.g. an image of a signature on the document) within an image. Imaging barcode scanners, despite being equipped with image sensors, may be unsuitable for document capture operations, as they are often adapted specifically for barcode capture.

More specifically, in some imaging barcode scanners, the field of view of an image sensor may be split by mirror assemblies into two or more distinct fields of view having different angles. As a result, the individual split fields of view have reduced resolutions in comparison with the resolution of the image sensor itself Reduced resolution can impede accurate document capture. Further, due to the divergent angles of the split fields of view, each individual field of view may not capture the entirety of a document placed on the scanner. These issues may be overcome by employing larger, higher-resolution image sensors; however, larger sensors can lead to an undesirable increase in cost of the scanner, and can also impose a greater computational burden on the scanner (due to the larger volume of data contained in the captured images).

Another approach to providing both barcode capture and document capture is to provide both an imaging barcode scanner and a document scanner. However, such implementations also incur additional costs, and can result in crowding, particularly in point-of-sale applications where various other devices are already present (e.g. monitor, cash drawer, printer, payment card reader, and the like). Accordingly, there is a need for an imaging barcode scanner for enhanced document capture.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
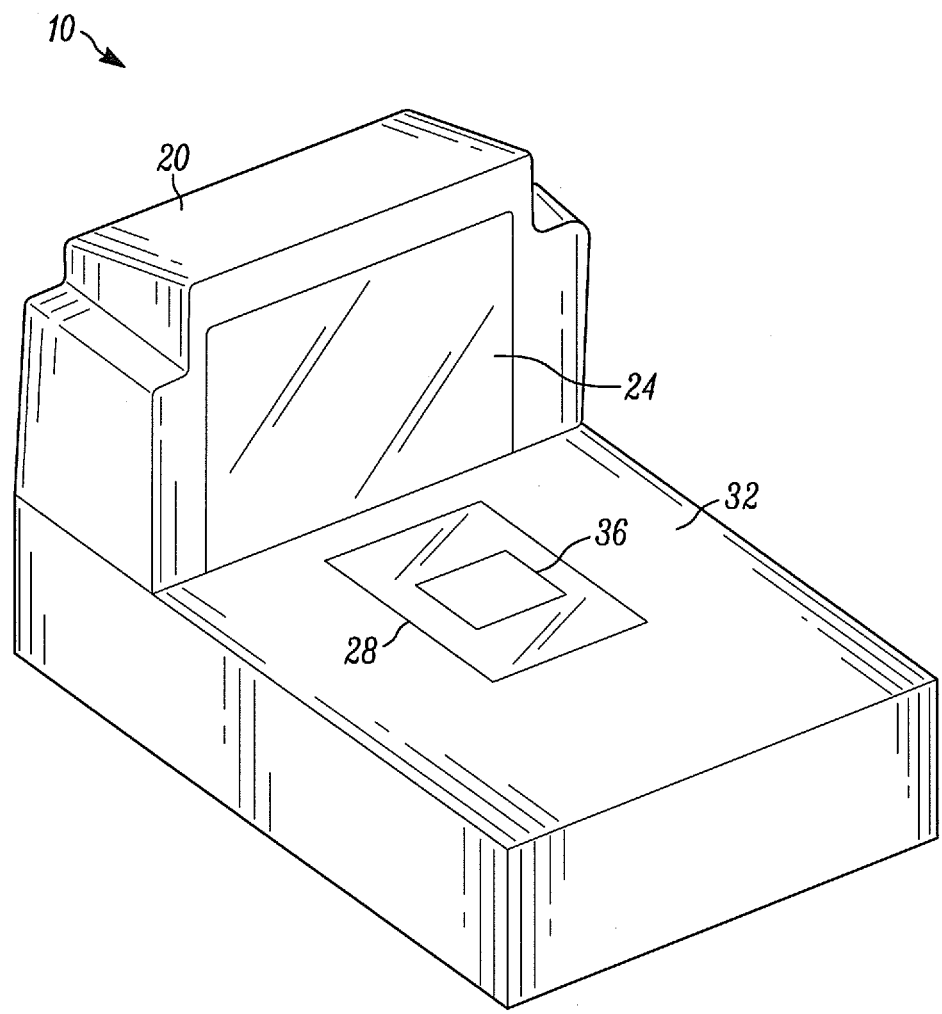
FIG. 1 depicts a bioptic scanner in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

According to some aspects of the specification, an imaging barcode scanner is provided. The imaging barcode scanner includes a housing defining a work surface, a window supported by the housing, a first array of photosensitive elements having a first field of view traversing the window and intersecting the work surface at a first angle, and a second array of photosensitive elements having a second field of view traversing the window and intersecting the work surface at a second angle. The imaging barcode scanner also includes a processor connected to the first and second arrays of photosensitive elements, and configured to: receive a first image of the work surface from the first array of photosensitive elements, and a second image of the work surface from the second array of photosensitive elements; register the first image with the second image; and generate an enhanced image of the work surface based on the registered first image and second image, the enhanced image having a greater pixel density than the first image and the second image.

According to further aspects of the specification, a method is provided in an imaging barcode scanner having a housing defining a work surface, and a window supported by the housing. The method comprises: at a processor, receiving a first image of the work surface from a first array of photosensitive elements having a first field of view traversing the window and intersecting the work surface at a first angle; at the processor, receiving a second image of the work surface from a second array of photosensitive elements having a second field of view traversing the window and intersecting the work surface at a second angle; at the processor, registering the first image with the second image;

and at the processor, generating an enhanced image of the work surface based on the registered first image and second image, the enhanced image having a greater pixel density than the first image and the second image.

FIG. 1 depicts an imaging barcode scanner, such as a bioptic imaging scanner 10 (also referred to herein as the "scanner 10"). The scanner 10 includes a housing 20 supporting various other components, certain of which are discussed herein. The housing 20 supports an upright window 24 and a lower window 28. In the present embodiment, the upright window 24 is generally vertical, and the lower window 28 is generally horizontal. In other embodiments, however, the upright window 24 and the lower window 28 can be supported by housing 20 at other angles of inclination. The lower window 28 forms at least part of a work surface 32 on which objects to be imaged are placed. The housing 20 can be integrated into a point-of-sale (POS) counter (not shown), although in some embodiments housing 20 may be a stand-alone device. Scanner 10 can be employed to capture images of, for example, a document 36 (e.g. a driver's license, check, packing slip, or the like) placed on the work surface 32 (in the present example, the document 36 is placed on the lower window 28 within the work surface 32) either face-up or face-down. As will be discussed herein, the scanner 10 includes certain components permitting an enhanced image of the document 36 to be generated from a plurality of images having pixel densities lower than the pixel density of the enhanced image.

Figure 2:
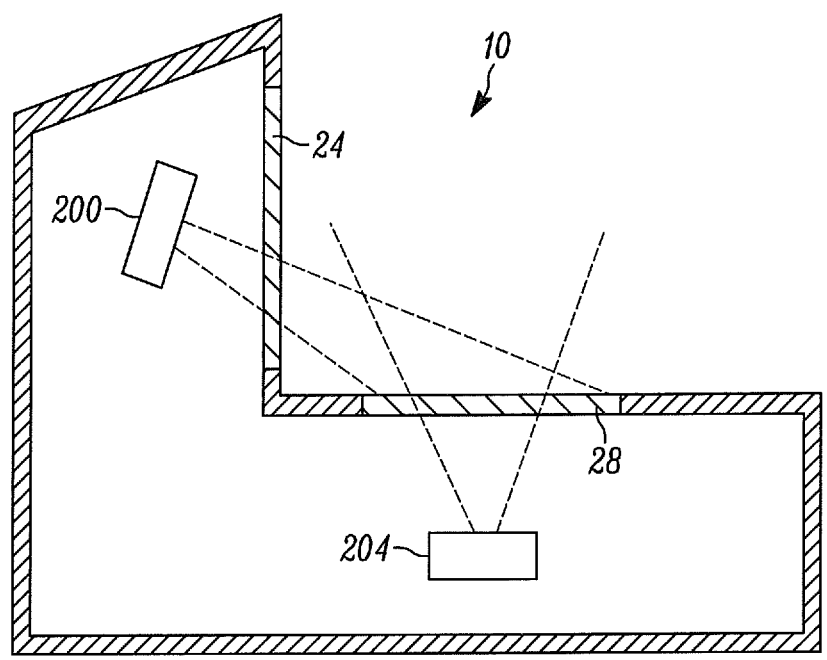
FIG. 2 is a cross-sectional schematic view of the bioptic scanner of FIG. 1 that includes a plurality of solid-state image sensors in accordance with some embodiments.

Referring now to FIG. 2, a schematic cross-sectional view of the scanner 10 is shown, revealing certain internal components of the scanner 10. In particular, housing 20 contains at least a first imaging sensor 200 and a second imaging sensor 204 (as will become apparent below, additional imaging sensors may also be provided). The imaging sensors 200 and 204 are mounted within the housing 20 adjacent to the upright window 24 and the lower window 28, respectively. As will be discussed in greater detail below, the fields of view of the imaging sensors 200 and 204 can be split, for example by one or more mirrors, into a plurality of distinct fields of view. In other words, each of the imaging sensors 200 and 204 may provide not one, but a set of fields of view. The fields of view emanating from a given imaging sensor may partially overlap with each other to varying degrees. The fields of view of the imaging sensor 200 traverse the upright window 24 (at different angles, due to the above-mentioned mirrors), and the fields of view of the imaging sensor 204 traverse the lower window 28 (again, at different angles, due to the above-mentioned mirrors). As seen in FIG. 2, the fields of view of the imaging sensors 200 and 204 may intersect with each other. The scanner 10 can also include illumination components (not shown) in some embodiments.

As mentioned above, the imaging sensors 200 and 204 each have a plurality of fields of view. To that end, each of the image sensors 200 and 204 includes a plurality of arrays of photosensitive elements, with each array having a different field of view. For example, the image sensors 200 and 204 can each be a CCD or CMOS sensor, with the area of the sensor subdivided into the above-mentioned arrays. Optical elements such as mirrors can be used to direct the fields of view of each array of photosensitive elements. In other embodiments, the arrays can be physically oriented at different angles from each other. In still other embodiments, rather than being portions of an image sensor, each array of photosensitive elements can be provided by a separate image sensor. As noted above, the fields of view of a given image sensor may overlap to varying degrees, but do not necessarily intersect. For example, the image sensor 200 may be subdivided into three arrays, each with a distinct field of view. The first and third fields of view may both overlap with the second field of view, but may not overlap with each other. In other words, it is possible, although not necessary, that no single field of view captures the entirety of the work surface 32, or the entirety of the window 28.

Figure 3:
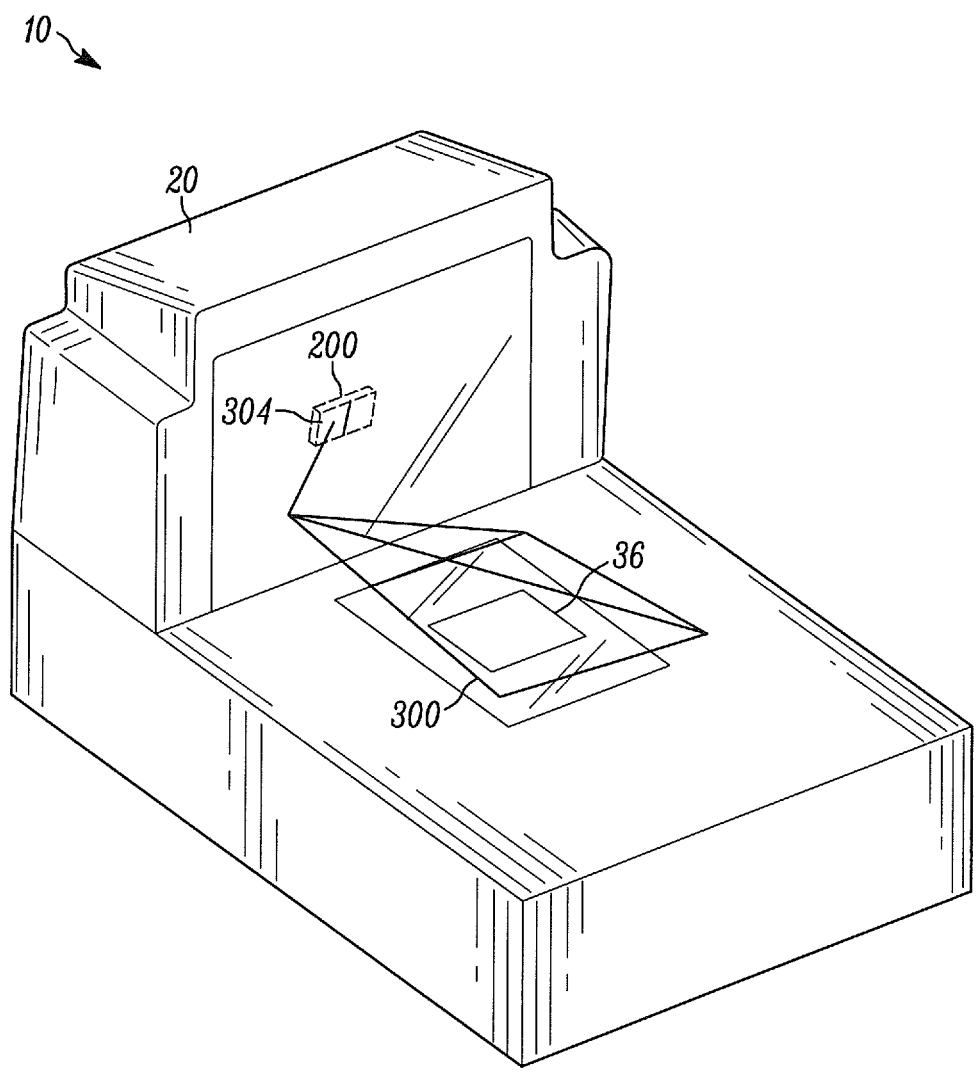
FIG. 3 depicts the bioptic scanner of FIG. 1 with a schematic of a first field of view in accordance with some embodiments.
Figure 4:
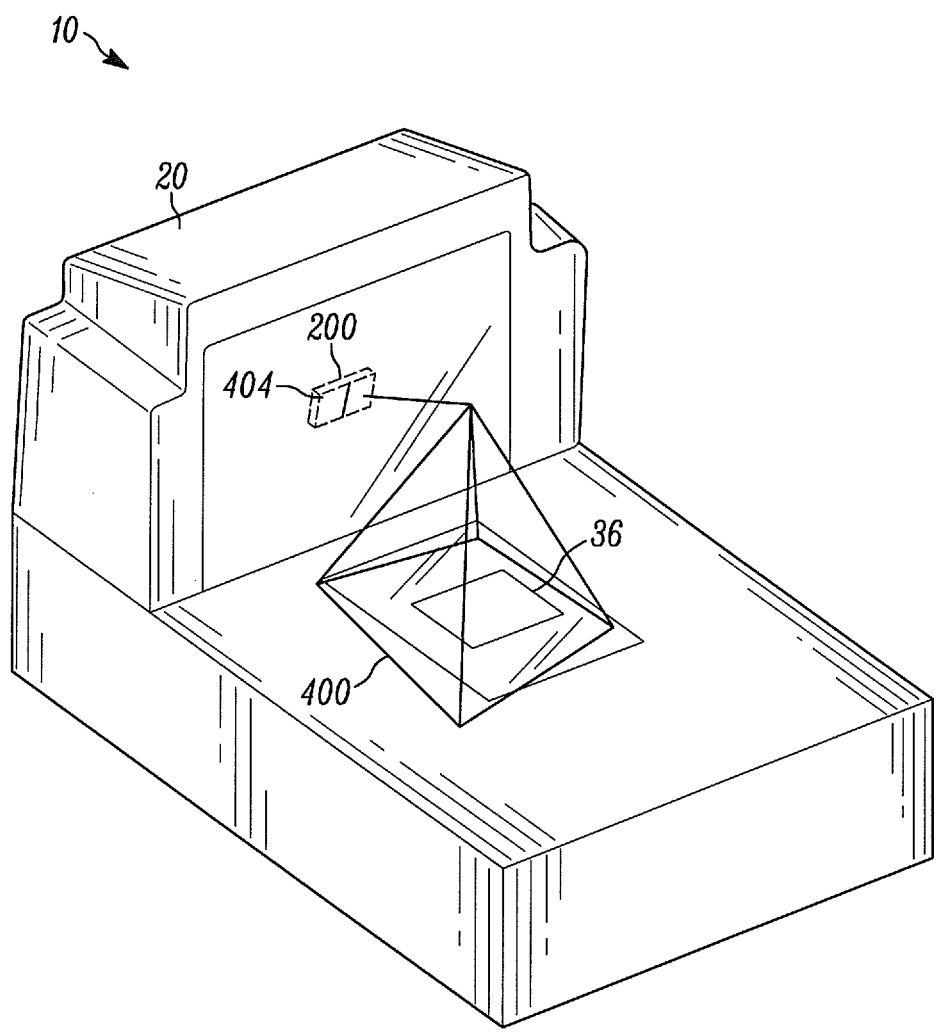
FIG. 4 depicts the bioptic scanner of FIG. 1 with a schematic of a second field of view in accordance with some embodiments.

FIG. 3 depicts a first field of view 300 of a first array 304 of photosensitive elements. The first array 304 consists of a portion of the image sensor 200 (in particular, one half of the imaging surface of the image sensor 200) in the present example. FIG. 4 depicts a second field of view 400 of a second array 404 of photosensitive elements, which in the present example consists of the remainder of the image sensor 200 (that is, the portion of the image sensor 200 not included in the first array 304). As seen in FIGS. 3 and 4, the fields of view 300 and 400 are redirected (e.g. by one or more mirrors, not shown) to intersect the work surface 32 at different angles from each other, although both fields of view 300 and 400 encompass the document 36. In other embodiments, additional fields of view, at further angles, can be provided by further subdividing the photosensitive elements of the image sensor 200, or by providing additional image sensors, or by a combination of additional image sensors and additional subdivisions of image sensor 200. In the present embodiment, the image sensor 204 disposed below the lower window 28 is subdivided similarly to the images sensor 200. The image sensor 204 can also be further subdivided, supplemented by additional image sensors, or both. In another example embodiment, each of the image sensors 200 and 204 is subdivided into three arrays of photosensitive elements, each with a distinct field of view impacting the work surface 32 at a distinct angle.

As will now be apparent to those skilled in the art, the arrays 304 and 404, when capturing images of the work surface 32, generate image data defining different portions of the work surface 32 at different levels of detail, due to the angles of the fields of view 300 and 400. The scanner 10 is configured to capture images of the work surface 32 using each of the above-mentioned arrays, and to generate an enhanced image based on the captured images. The enhanced image is also referred to as a "super-resolution" image, and has a higher pixel density than either of the captured images. That is, the enhanced image has a higher resolution than the captured images despite depicting an area of the work surface 32 that is the same size as, or smaller than, the area depicted by either captured image.

Before describing the generation of an enhanced image by the scanner 10 in detail, certain internal components of the scanner 10 will be discussed with reference to FIG. 5.

The scanner 104 includes a processor 500 interconnected with a memory 504. The processor 500 and the memory 504 can each comprise one or more integrated circuits (IC). The processor 500 runs or executes operating instructions or applications that are stored in the memory 504 to perform various functions for the scanner 10, including the processing of image data to generate the above-mentioned super-resolution images. The processor 500, and the scanner 10, are therefore said herein to be "configured" to perform certain actions. The processor 500 can include one or more microprocessors, microcontrollers, digital signal processors (DSP), state machines, logic circuitry, or any device or devices that process information based on operational or programming instructions stored in the memory 504. The memory 504 can include any one of, or any suitable combination of, storage technologies, including magnetic hard disks, flash memory, and the like.

Among the applications stored in the memory 504 is an enhanced document capture application 508 (also referred to herein as the application 508). The application 508 contains a plurality of computer-readable instructions that are executable by the processor 500. When the processor 500 executes the instructions of the application 508, the processor 500 performs various actions, and controls the other components of the scanner 10 (e.g. the image sensors 200 and 204) to perform certain actions. In particular, as will be discussed in detail below, the processor 500 is configured to generate an enhanced image of the work surface 32 via the execution of the application 508 and the control of the scanner 10's other components.

Figure 5:
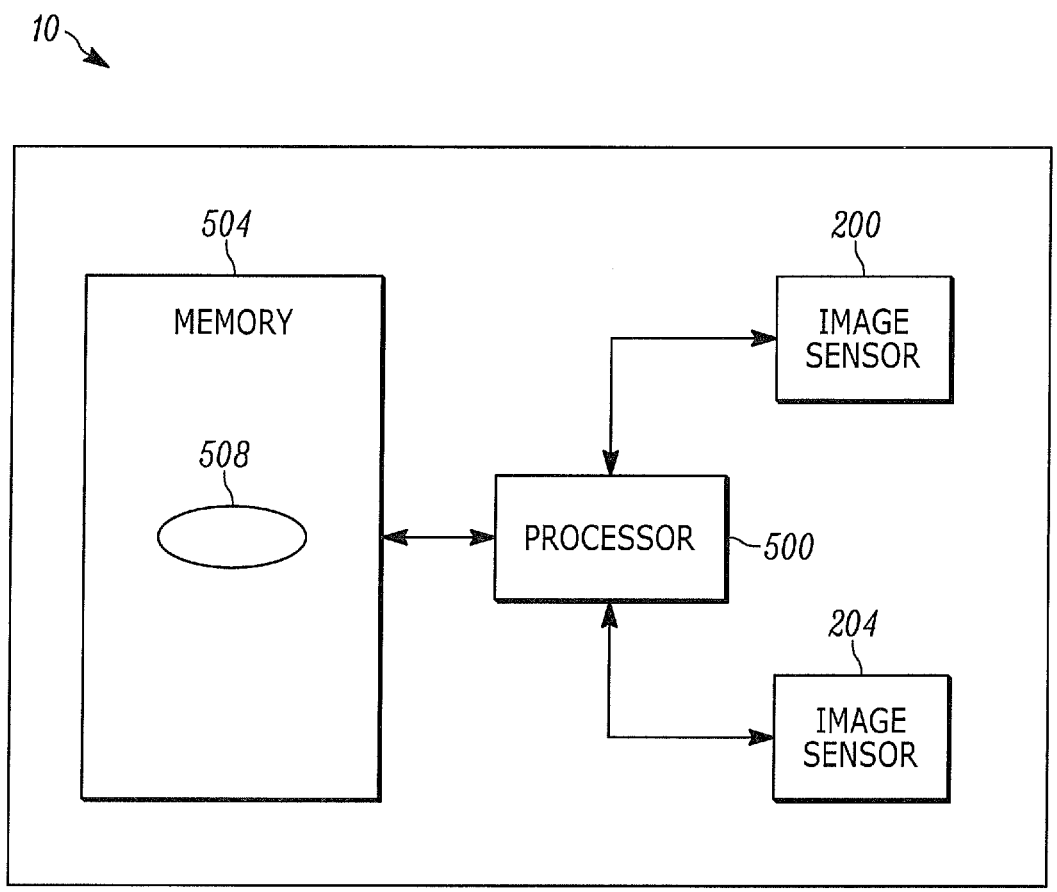
FIG. 5 is a schematic of certain internal components of the bioptic scanner of FIG. 1 in accordance with some embodiments.

Also shown in FIG. 5 are the image sensors 200 and 204, interconnected with the processor 500. In some embodiments, the scanner 10 can include additional components (not shown) such as a network interface for communicating with other devices such as a point-of-sale computer, a display, a speaker and the like. The components of the scanner 10 can be contained within the housing 20, which can be constructed of any suitable material, or combination of materials (e.g. plastics, metals, and the like).

Figure 6:
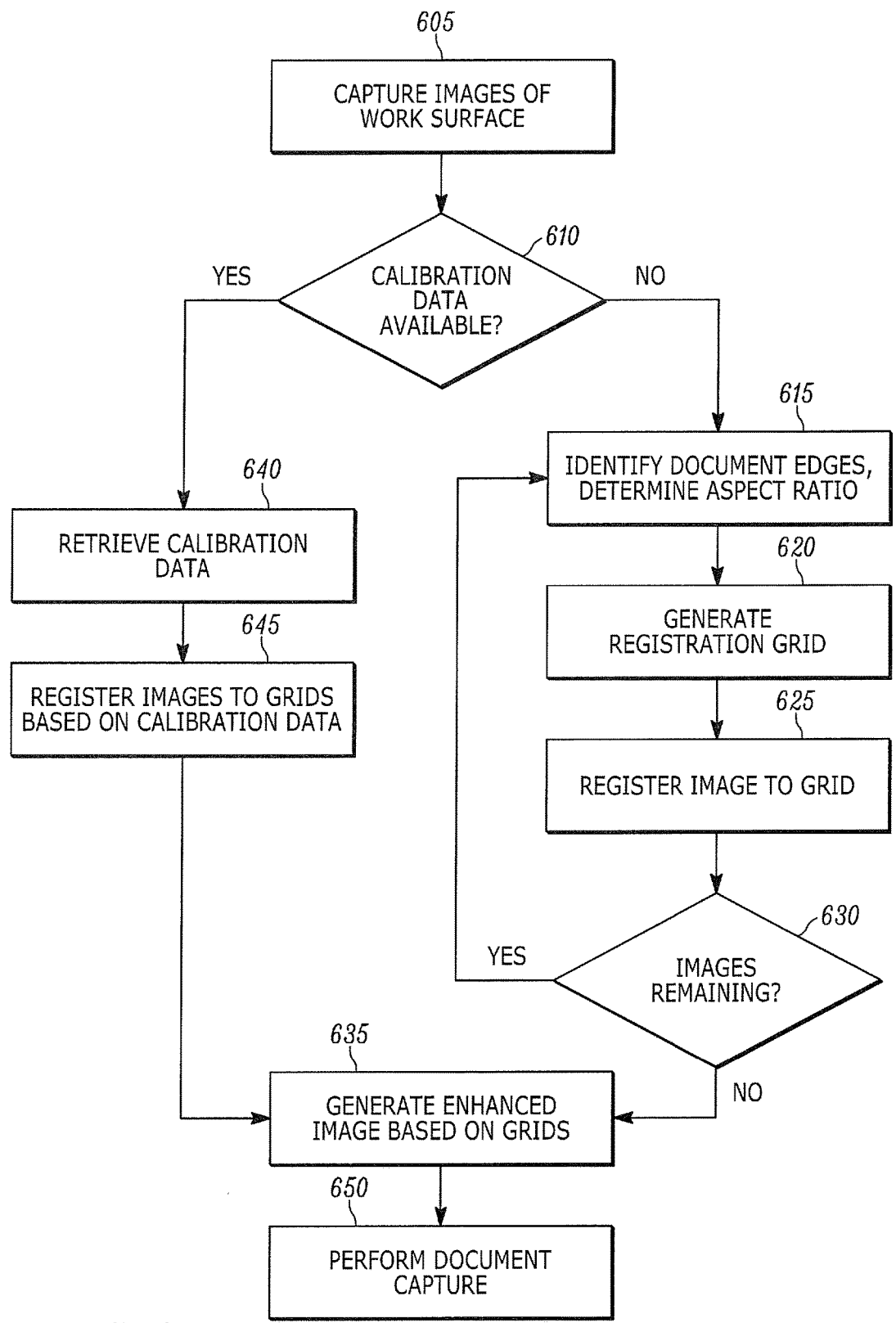
FIG. 6 depicts a method of generating an enhanced image in the scanner of FIG. 1 in accordance with some embodiments.

Turning now to FIG. 6, a method 600 of generating an enhanced image of the work surface 32 is depicted. The method 600 will be described below in conjunction with its performance in the scanner 10. In particular, the blocks of the method 600 are performed by the processor 500, via the execution of the instructions contained within the application 508.

At block 605, the scanner 10 is configured to capture images of the work surface 32. In the present example performance of the method 600, the processor 500, via execution of the application 508, controls the image sensor 200 to capture two images of the work surface 32 (a first image being captured by the first array 304, and a second image being captured by the second array 404). In other example performances of the method 600, the processor 500 can also control the image sensor 204 to capture an additional two images. In further performances of the method 600, the processor 500 can activate both image sensors 200 and 204 to capture a total of four images of the work surface 32 (two images depicting the "top" of the work surface 32 visible in FIG. 1, and two images depicting the underside of the work surface 32). When only one set of arrays is activated at block 605, the processor 500 can be configured to determine which set of arrays (e.g. the arrays of the image sensor 200 or the arrays of the image sensor 204) by capturing an initial image with each image sensor and determining which side of the document 36 contains text (rather than being blank). The images captured at block 605 are stored in the memory 504.

Figure 7:
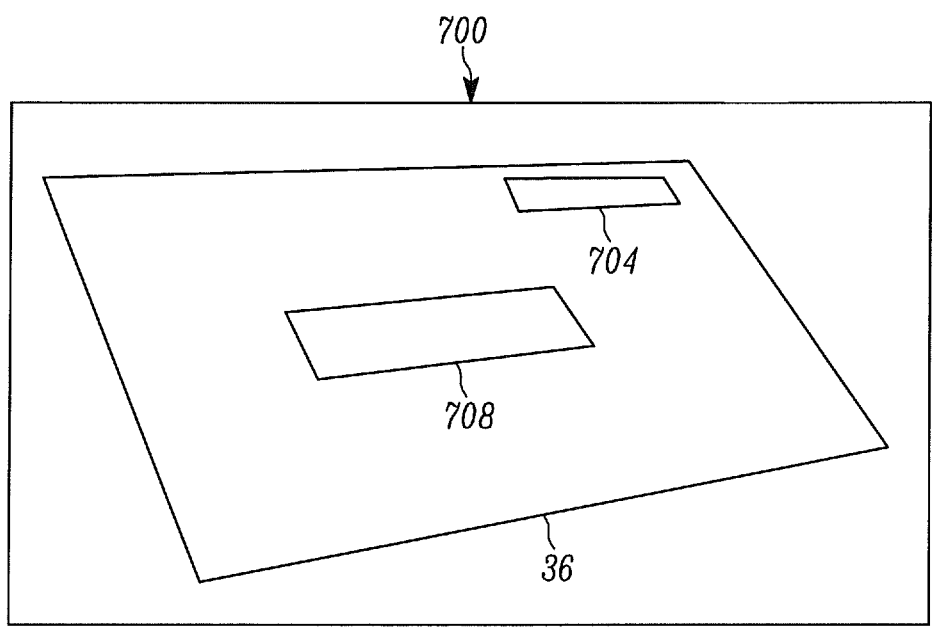
FIG. 7 depicts a first image captured by the scanner of FIG. 1 during the performance of the method of FIG. 6 in accordance with some embodiments.
Figure 8:
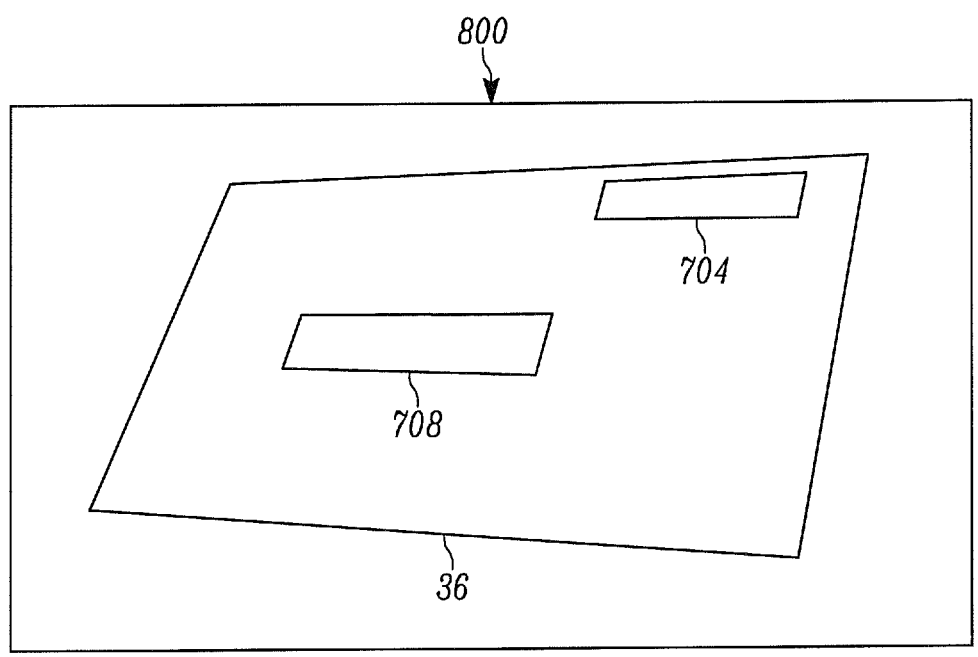
FIG. 8 depicts a second image captured by the scanner of FIG. 1 during the performance of the method of FIG. 6 in accordance with some embodiments.

FIGS. 7 and 8 depict examples of images captured by the first array 304 and the second array 404, respectively, of the image sensor 200. FIG. 7 shows an image 700 depicting the document 36, which bears various elements, such as a bar code 704 and a block of text 708, such as an address, a signature or the like. A wide variety of other elements (text, images and the like) may also be present on the document 36 and depicted in the image 700.

FIG. 8 shows an image 800 depicting the document 36 from an angle different from the angle shown in FIG. 7. Thus, the barcode 704 and the text 708 are also visible in the image 800, although they are distorted differently from the depictions of the barcode 704 and the text 708 in the image 700. The differing distortions visible in FIGS. 7 and 8 result from the different angles of the fields of view 300 and 400.

Returning to FIG. 6, having captured the images at block 605, at block 610 the scanner 10 is configured to determine whether calibration data is available. In some embodiments, calibration data may be stored in the memory 504, defining a mapping between the pixels of any images captured by the image sensors 200 and 204 and the physical area of the work surface 32. In other words, the installed positions of the image sensors 200 and 204 may be known to a suitably high degree of accuracy that it is known in advance which portion of the work surface 32 is depicted by each pixel in an image captured by, for example, array 304. In the present embodiment, it is assumed that calibration data is not present, and the determination at block 610 is therefore negative.

Following a negative determination at block 610, the performance of the method 600 proceeds to block 615, at which the scanner 10 is configured to select any one of the captured images. The scanner 10 is then configured to identify the edges of the document 36 in the selected image and determine the aspect ratio of the edges (that is, the ratio of the document's length to the document's width, assuming the document 36 is rectangular). Edge detection and ratio calculation may be performed according to conventional techniques.

At block 620, based on the ratio of the sides of the document 36, the scanner 10 is configured to generate a rectangular registration grid corresponding to the document 36, which is assumed to lie on the same plane as the work surface 32. For example, if the ratio of the document sides was determined to be 7:4 at block 615, a rectangular grid having the same 7:4 aspect ratio is generated at block 620. The resolution of the grid generated at block 620 is not particularly limited, but in general has a pixel at least as great as the image captured at block 605. For example, if one side of the document 36 is depicted by 400 pixels in the image 700, the corresponding side of the grid generated at block 620 may have 450 pixels. In addition, the grid generated at block 620 preferably contains twice the linear number of pixels (that is, four times the total number of pixels) as the portion of the image 700 depicting the document 36.

Figure 9:
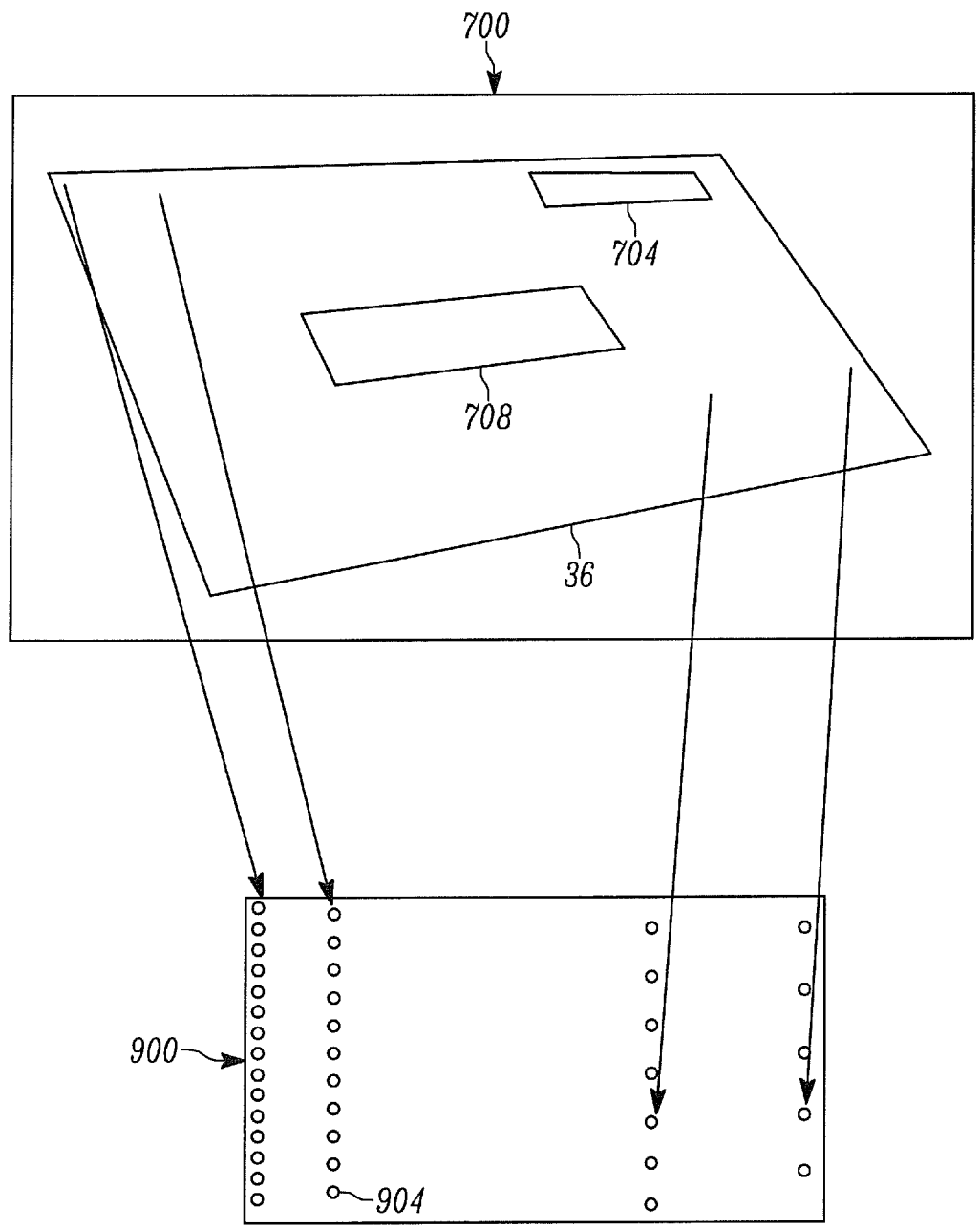
FIG. 9 depicts a first grid generated by the scanner of FIG. 1 based on the image of FIG. 7 in accordance with some embodiments.

At block 625, having generated a grid for the selected image, the scanner 10 is configured to register the selected image to the grid. In other words, the scanner 10 is configured to project each pixel falling within the detected edges of the document 36 in the captured image (e.g. the image 700) onto a corresponding position in the grid. Referring to FIG. 9, an example grid 900 is illustrated, and certain columns of pixels 904 are illustrated as having been projected from the image 700 onto grid 900 (the other columns of pixels have been omitted for illustrative purposes). As seen in FIG. 9, due to the angle of the field of view 300, a greater number of pixels depict the left edge of the document 36 than the right edge, and thus the grid 900 is less densely populated with image data at one side than the other.

Arrows are used in FIG. 9 to illustrate the projection of four sample pixels from the image 700 onto the grid 900. As shown by the arrows, the pixels projected from the image 700 are placed on the grid 900 at positions corresponding to the position of the original pixel relative to the document 36 within the image 700. Thus, at block 625 a grid is generated that corresponds to the physical shape of the document 36, and a portion of the image data from the image 700 is mapped onto the grid 900. In other words, the image 700 is registered to the grid 900, which represents a portion of the work surface 32 (specifically, the portion of the work surface 32 occupied by the document 36). The grid 900, once pixels from the image 700 have been projected onto it, therefore represents an undistorted view of the document 36 extracted from the image 700.

Returning to FIG. 6, at block 630 the processor 500 is configured to determine whether any images remain to be processed. In the present example performance of the method 600, the determination is affirmative, because the image 800 has not yet been registered to a grid. Therefore, the scanner 10 repeats the performance of blocks 615, 620 and 625 with respect to the image 800. The results of performing blocks 615, 620 and 625 in connection with the image 800 are shown in FIG. 10.

Figure 10:
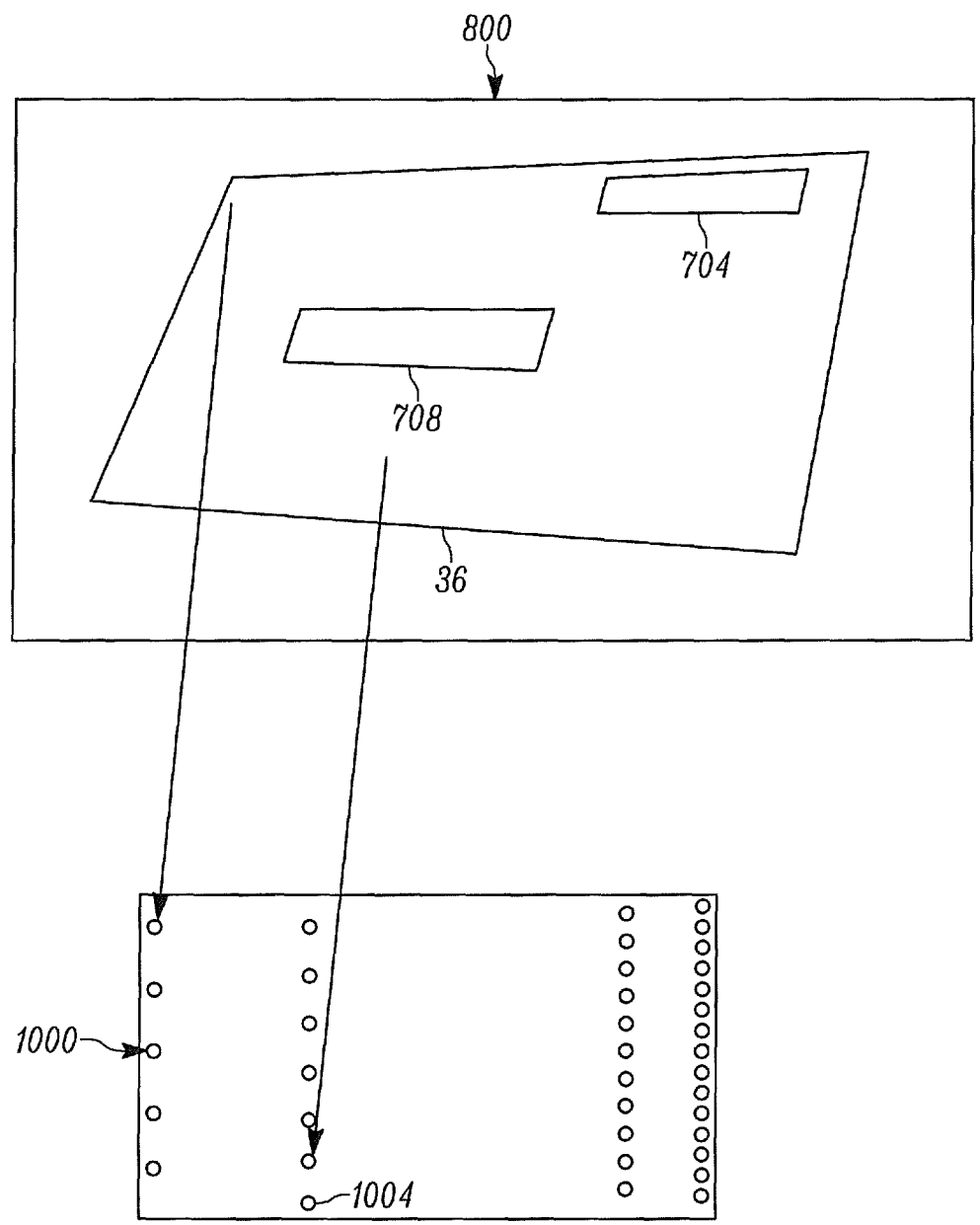
FIG. 10 depicts a first grid generated by the scanner of FIG. 1 based on the image of FIG. 8 in accordance with some embodiments.

FIG. 10 depicts the image 800, as well as a grid 1000 generated based on the detected ratio of the document 36's edges in the image 800. As will now be apparent to those skilled in the art, the dimensions of the grid 1000 are close to, or identical to, the dimensions of the grid 900. Four sample columns of the grid 1000 are shown populated with pixels from the image 700, and the remaining columns of pixels are omitted for ease of illustration. As seen in FIG. 10, the pixel density of the completed grid 1000 also varies, but in a direction opposite to the pixel density of the grid 900. Due to the different angles of the fields of view 300 and 400, the images 700 and 800 provide varying levels of detail at different portions of the document 36.

In a second performance of block 630, the determination is negative in the present example, as both the images 700 and 800 have been registered to grids. In other embodiments with a larger number of arrays of photosensitive elements, additional repetitions of blocks 615-630 may be performed until all images captured at block 605 have been registered to respective grids.

Figure 11:
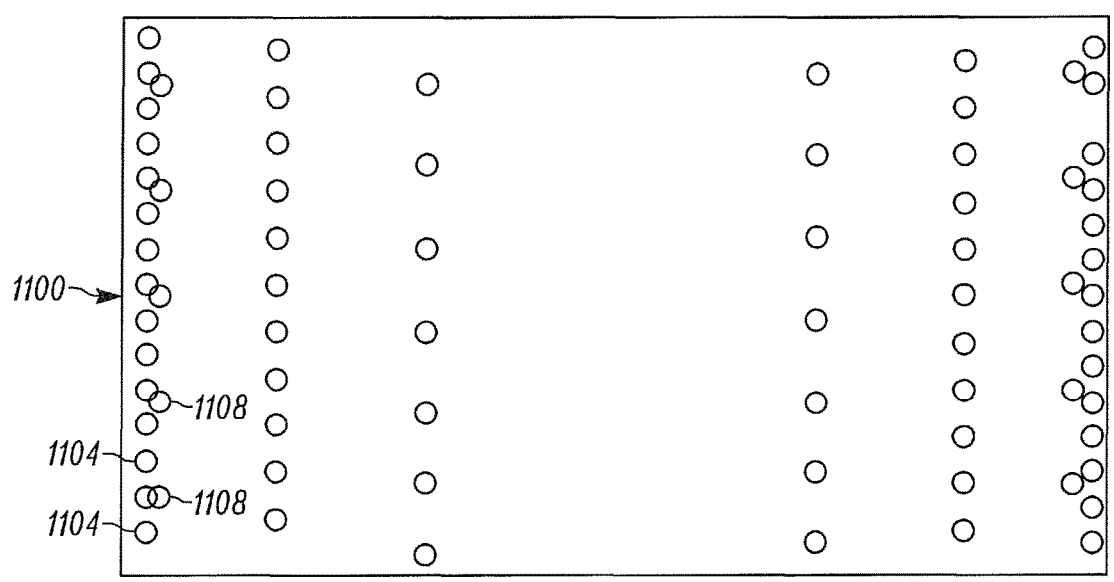
FIG. 11 depicts an overlay of the grids of FIGS. 9 and 10 in accordance with some embodiments.

After a negative determination at block 630, the performance of the method 600 proceeds to block 635. At block 635, the processor 500 is configured to generate an enhanced image from the grids generated at previous performances of blocks 620 and 625. For illustrative purposes, FIG. 11 depicts a composite grid 1100 in which the sample pixels shown in grids 900 and 1000 have been overlaid (the omitted pixels from FIGS. 9 and 10 are still omitted in FIG. 11 for simplicity of illustration). As seen in FIG. 11, a column of pixels 1104 from the grid 900 and a column of pixels 1108 from the grid 1000 do not align with each other exactly. Instead, the pixels 1108 fill in gaps between the pixels 1104. Thus, it can be seen that a greater level of visual detail is available by combining the separate grids generated earlier in the method 600.

The generation of an enhanced image at block 635 comprises registering the separate grids (grids 900 and 1000) to each other, for example by performing known image registration techniques, such as feature identification. In other words, the images 700 and 800 (or at least the portions thereof representing the document 36) are registered with each other. This can result in a grid similar to that illustrated in FIG. 11. From the registered grids (e.g. the composite grid), the processor 500 is then configured to produce an enhanced image having greater accuracy and detail than either input image (that is, than either of the images 700 and 800). For example, the enhanced image can contain a new set of pixels with higher fidelity (i.e. corresponds more closely to the true appearance of the document 36) than could be achieved from either one of the input images 700 and 800. In some embodiments, only certain regions of the enhanced image may have such higher fidelity (for instance, the images 700 and 800 may overlap only partially; for non-overlapping regions, only one of the images 700 and 800 acts as a source for the enhanced image and it may not be possible to achieve higher fidelity for those regions).

The new set of pixels can be generated according to any conventional super-resolution technique, such as that described by Capel, D. and Zisserman, A., Super-resolution Enhancement of Text Image Sequences, *Proceedings of the 2000 International Conference on Image Processing* (ICIP 2000), the contents of which (available at www.robots.ox-.ac.uk/~vgg/publications/) are hereby incorporated by reference. In general, the generation of the higher-density set of pixels includes generating pixels that minimize total image variance (that is, minimize the differences between the new pixels and all the "original" pixels from the grids 900 and 1000). In other words, additional detail may be interpolated from the original images.

Figure 12:
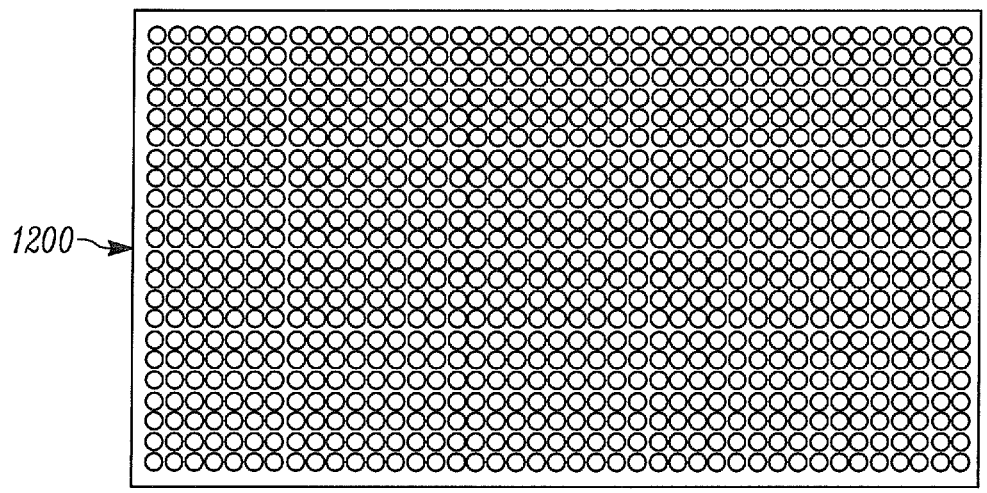
FIG. 12 depicts an enhanced image generated by the scanner of FIG. 1 in accordance with some embodiments.

FIG. 12 depicts the pixel grid of an enhanced image 1200 generated at block 625. As seen by comparing FIG. 12 with FIGS. 9 and 10, the pixel density of the enhanced image 1200 is greater than even the portions of the grids 900 and 1000 with the greatest pixel density. Therefore, the enhanced image 1200 depicts the document 36 at a greater level of detail than either of the images 700 and 800 captured at block 605.

Returning to FIG. 6, when the determination at block 610 is affirmative, the performance of blocks 615, 620 and 625 may be omitted, and the scanner 10 may instead perform block 640. At block 640, calibration data may be retrieved from the memory 504. The calibration data may be placed in the memory 504 by the manufacturer of the scanner 10, and may contain a grid definition for each array of photosensitive elements contained within the scanner 10. That is, the arrays (e.g. the arrays 304 and 404) may be installed at known locations relative to the work surface 32 with sufficiently small positional tolerances that it is known in advance what physical position of the work surface 32 is represented by each pixel of any image captured by each of the arrays 304 and 404.

Rather than generate grids, therefore, the scanner 10 may simply retrieve the calibration data and, at block 645, register the images to the grids defined by the calibration data with the corresponding pixels identified by the calibration data. For example, the calibration data may specify that the pixel having the coordinates (104, 282) in the image 700 is projected to the coordinates (0,0) in the grid 900. Similar mappings may be included for every other pixel in the image 700. Having performed blocks 640 and 645, the scanner 10 may proceed to block 635 as described above.

Once the enhanced image is generated at block 635, the enhanced image may be stored in the memory 504. The performance of the method 600 can also proceed to block 650, at which the scanner 10 is configured to perform a document capture operation on the enhanced image.

The nature of the document capture operation is not particularly limited. For example, the processor 500 may identify and decode the bar code 704 from the enhanced image 1200, and also identify and extract the text element 708. The scanner 10 may then, for example, be configured to transmit the extracted text element 708 to another computing device with the decoded bar code as an identifier for the text element 708.

Variations to the above are contemplated. For example, in some embodiments the scanner 10 may store lower-accuracy calibration data in the memory 504. Such data may be insufficiently precise to perform blocks 640 and 645 (and may therefore result in a negative determination at block 610), but may nevertheless be applied by the processor 500 at blocks 615 and 635 as boundaries on edge identification and feature registration.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. An imaging barcode scanner, comprising:
 a housing defining a work surface;
 a window supported by the housing;
 a first array of photosensitive elements having a first field of view traversing the window and intersecting the work surface at a first angle;
 a second array of photosensitive elements having a second field of view traversing the window and intersecting the work surface at a second angle different than the first angle; and
 a processor in communication with the first array of photosensitive elements and the second array of photosensitive elements, the processor configured to:
  receive a first image of the work surface from the first array of photosensitive elements and a second image of the work surface from the second array of photosensitive elements;
  register the first image with the second image by:
   generating a first grid corresponding to a document in the first image, the first grid having a first varying pixel density across the first grid resulting from the first angle of the first field of view;
   generating a second grid corresponding to the document in the second image, the second grid having a second varying pixel density across the second image resulting from the second angle of the second field of view; and
   registering a higher pixel density region of the first grid with a corresponding lower pixel density region of the second grid;
  generate an enhanced image of the work surface based on the registered first image and second image, the enhanced image having a greater pixel density than the first image and the second image.

2. The imaging barcode scanner of claim 1, the document being a planar, rectangular document on the work surface.

3. The imaging barcode scanner of claim 1, the processor configured to generate the enhanced image by minimizing variance between a subset of pixels contained within the first and second grids.

4. The imaging barcode scanner of claim 1, wherein the first array of photosensitive elements comprises a first image sensor, and wherein the second array of photosensitive elements comprises a second image sensor.

5. The imaging barcode scanner of claim 1, wherein the first array of photosensitive elements comprises a first portion of a first image sensor, and wherein the second array of photosensitive elements comprises a second portion of the first image sensor.

6. The imaging barcode scanner of claim 1, wherein the window comprises a lower window in the work surface, and an upright window adjacent to the work surface.

7. The imaging barcode scanner of claim 6, the first array of photosensitive elements and the second array of photosensitive elements being supported by the housing to define respective fields of view traversing the upright window and intersecting the work surface.

8. The imaging barcode scanner of claim 1, the processor configured to generate the enhanced image by additionally interpolating image data depicting portions of the work surface not depicted in either of the first image and the second image.

9. A method in an imaging barcode scanner having a housing defining a work surface, and a window supported by the housing, the method comprising:
at a processor, receiving a first image of the work surface from a first array of photosensitive elements having a first field of view traversing the window and intersecting the work surface at a first angle;
at the processor, receiving a second image of the work surface from a second array of photosensitive elements having a second field of view traversing the window and intersecting the work surface at a second angle different than the first angle;
at the processor, registering the first image with the second image;
at the processor, generating an enhanced image of the work surface based on the registered first image and second image, the enhanced image having a greater pixel density than the first image and the second image; and
wherein registering the first image with the second image comprises:
generating a first grid corresponding to a document in the first image, the first grid having a first varying pixel density across the first grid resulting from the first angle of the first field of view,
generating a second grid corresponding to the document in the second image, where the second grid has a second varying pixel density across the second grid resulting from the second angle of the second field of view, and
registering a higher pixel density region of the first grid with a corresponding lower pixel density region of the second grid.

10. The method of claim 9, the document being a planar, rectangular document on the work surface.

11. The method of claim 9, wherein generating the enhanced image comprises minimizing variance between a subset of pixels contained within the first and second grids.

12. The method of claim 9, wherein the first array of photosensitive elements comprises a first image sensor, and wherein the second array of photosensitive elements comprises a second image sensor.

13. The method of claim 9, wherein the first array of photosensitive elements comprises a first portion of a first image sensor, and wherein the second array of photosensitive elements comprises a second portion of the first image sensor.

14. The method of claim 9, wherein the window comprises a lower window in the work surface, and an upright window adjacent to the work surface.

15. The method of claim 14, further comprising:
receiving the first image through the upright window as established by the first field of view for the first array of photosensitive elements; and
receiving the second image through the lower window as established by the second field of view of the second array of photosensitive elements.

16. The method of claim 9, further comprising:
generating the enhanced image at the processor by additionally interpolating image data depicting portions of the work surface not depicted in either of the first image and the second image.

17. An imaging barcode scanner, comprising:
a housing defining a work surface and having a window;
a first array of photosensitive elements having a first field of view traversing the window and intersecting the work surface at a first angle;
a second array of photosensitive elements having a second field of view traversing the window and intersecting the work surface at a second angle different than the first angle; and
a processor in communication with the first array of photosensitive elements and the second array of photosensitive elements, the processor configured to:
receive a first image of the work surface from the first array of photosensitive elements and at the first angle;
receive a second image of the work surface from the second array of photosensitive elements and at the second angle;
identify a first grid corresponding to a document identified in the first image, the first grid having a varying pixel density in a first direction;
identify a second grid corresponding to the document identified in the second image, the second grid having a varying pixel density in a second direction different than the first direction;
register the first grid to the second grid by registering a higher pixel density portion of the first image and a corresponding lower pixel density portion of the second image; and
generate an enhanced image of the work surface based on the registered first image and second image, the enhanced image having a greater pixel density than the first image and the second image.

* * * * *